(12) United States Patent
O'Connor et al.

(10) Patent No.: US 7,037,254 B2
(45) Date of Patent: *May 2, 2006

(54) CONTROLLED ENVIRONMENT DEVICE

(76) Inventors: Michael O'Connor, 10953 Wilkinson Ave., Cupertino, CA (US) 95014; Marion E. Cox, 15906 Concord Cir., Morgan Hill, CA (US) 95037

( * ) Notice: Subject to any disclaimer, the term of this patent is extended or adjusted under 35 U.S.C. 154(b) by 0 days.

This patent is subject to a terminal disclaimer.

(21) Appl. No.: 10/729,632

(22) Filed: Dec. 5, 2003

(65) Prior Publication Data

US 2004/0116770 A1    Jun. 17, 2004

Related U.S. Application Data

(63) Continuation of application No. 09/972,236, filed on Oct. 5, 2001, now Pat. No. 6,685,622.

(60) Provisional application No. 60/241,382, filed on Oct. 17, 2000.

(51) Int. Cl.
*A61G 10/02* (2006.01)

(52) U.S. Cl. ............................................. 600/21; 312/1

(58) Field of Classification Search ................. 600/21; 312/1, 223.1; 62/51.1; 128/205.26, 897, 128/849, 846, 852, 842, 898; 134/199, 200, 134/61; 602/42, 53, 2; 422/1; 2/457; 454/57, 454/56; 604/20, 307, 289; 607/149, 153, 607/114; 606/135; 453/3; 428/76
See application file for complete search history.

(56) References Cited

U.S. PATENT DOCUMENTS

| | | | | |
|---|---|---|---|---|
| 1,251,258 A | * | 12/1917 | Magill | .................. 606/135 |
| 1,775,442 A | * | 9/1930 | Sarason | .................. 607/114 |
| 2,493,155 A | * | 1/1950 | McMillan | .................. 604/20 |
| 3,450,450 A | * | 6/1969 | Harris et al. | .................. 312/1 |
| 3,874,387 A | * | 4/1975 | Barbieri | .................. 602/53 |
| 4,026,286 A | * | 5/1977 | Trexler | .................. 128/205.26 |
| 4,059,903 A | * | 11/1977 | Piet et al. | .................. 312/1 |
| 4,089,571 A | * | 5/1978 | Landy | .................. 312/1 |
| 4,111,753 A | * | 9/1978 | Folsom et al. | .................. 435/3 |
| 4,262,091 A | | 4/1981 | Cox | |

(Continued)

FOREIGN PATENT DOCUMENTS

EP    0710172 B1 * 10/2000

OTHER PUBLICATIONS

Barazzone et al., "Oxygen toxicity in mouse lung: pathways to cell death," Am. J. Respir. Cell Mol. Biol., 19:573-581 [1998].

(Continued)

*Primary Examiner*—John P. Lacyk
(74) *Attorney, Agent, or Firm*—Medlen & Carroll LLP (57) ABSTRACT

The present invention relates to devices and methods for providing controlled environments for surgical procedures, as well as transplantation and wound healing. In particular, one embodiment of the present invention provides devices and methods to provide an anaerobic environment for incision sites. In other embodiments, the present invention provides devices and methods to maintain anaerobic conditions during the collection, transport, and implantation of organs, tissues, cells, and other transplant material. In further embodiments, the present invention provides devices and methods for the production and maintenance of an anaerobic environment surrounding sites of trauma or tissue injury. In particular, the present invention provides devices and methods which allow the operator to strictly control the environment for surgical procedures, transplantation and wound healing, etc. Thus, the present invention also finds use in specialized settings where hyperoxic conditions are desireable.

19 Claims, 4 Drawing Sheets

U.S. PATENT DOCUMENTS

| | | | | | |
|---|---|---|---|---|---|
| 4,275,719 | A | * | 6/1981 | Mayer | 128/847 |
| 4,366,809 | A | * | 1/1983 | Trexler | 600/21 |
| 4,367,728 | A | * | 1/1983 | Mutke | 600/21 |
| 4,376,437 | A | * | 3/1983 | Sundheim et al. | 602/2 |
| 4,550,713 | A | * | 11/1985 | Hyman | 600/21 |
| 4,566,293 | A | * | 1/1986 | Arner et al. | 62/51.1 |
| 4,612,916 | A | * | 9/1986 | Akers et al. | 600/21 |
| 4,701,415 | A | * | 10/1987 | Dutton et al. | 435/286.6 |
| 4,903,710 | A | * | 2/1990 | Jessamine et al. | 128/849 |
| 4,931,333 | A | * | 6/1990 | Henry | 428/76 |
| 4,950,222 | A | * | 8/1990 | Scott et al. | 600/21 |
| 4,960,143 | A | * | 10/1990 | Dore et al. | 134/199 |
| 5,095,925 | A | * | 3/1992 | Elledge et al. | 134/61 |
| 5,169,217 | A | * | 12/1992 | Orchard et al. | 312/223.1 |
| 5,316,541 | A | * | 5/1994 | Fischer | 600/21 |
| 5,352,414 | A | * | 10/1994 | Rothenberg | 422/101 |
| 5,380,077 | A | * | 1/1995 | Puschner et al. | 312/1 |
| 5,636,643 | A | * | 6/1997 | Argenta et al. | 128/897 |
| 5,727,569 | A | * | 3/1998 | Benetti et al. | 128/898 |
| 5,730,777 | A | * | 3/1998 | Petersen et al. | 95/12 |
| 6,184,035 | B1 | * | 2/2001 | Csete et al. | 435/377 |
| 6,402,724 | B1 | * | 6/2002 | Smith et al. | 604/289 |

OTHER PUBLICATIONS

Cargnoni et al., Changes in oxidative stress and cellular redox potential during myocardial storage for transplantation: experimental studies, J. Heart Lung Transplant., 18:478-487 [1999].

Ihnken et al., "Studies of hypoxemic/reoxygenation injury: without aortic clamping," J. Thorac. Cardiovasc. Surg., 110:1171-1181 [1995].

Ihnken et al., "Normoxic cardiopulmonary bypass reduces oxidative myocardial damage and nitric oxide during cardiac operations in the adult," J. Thorac. Cardiovasc. Surg., 116:327-334 [1998].

Knight, "Free radicals: their history and current status in aging and disease," Ann. Clin. Lab. Sci., 28:331-346 [1998].

Morita et al., "Studies of hypoxemic/reoxygenation injury: without aortic clamping," J. Thorac. Cardiovasc. Surg., 110:1235-1244 [1995].

Pepper et al., "Sequential oxidative damage, and changes in iron-binding and iron-oxidising plasma antioxidants during cardiopulmonary bypass surgery," Free Rad. Res., 21:377-385 [1994].

Satoh et al., "Oxygen toxicity induces apoptosis in neuronal cells," Cell. Mol. Nerurobiol., 18:649-666 [1998].

Sellke et al., "Twenty-four-hour heart preservation using continuous cold perfusion and copper (II) complexes," J. Surg. Res., 80:171-176 [1998].

Tian et al., "Alterations of antioxidant enzymes and oxidative damage to macromolecules in different organs or rats during aging," Free Radical Biol. Med., 24:1477-1484 [1998].

Williams et al., "Postoperative lung injury and oxidative damage in patients undergoing pulmonary resection," Eur. Respir. J., 11:1028-1034 [1998].

Capellier et al., "Oxygen tolerance in patients with acute respiratory failure," Intensive Care Med 24:422-428 [1998].

Folz et al., "Extracellular superoxide dismutase in the airways of transgenic mice reduces inflammation and attenuates lung toxicity following hyperoxia," J. Clin. Invest. 103:1055-1066 [1999].

Fridovich, "Oxygen toxicity: a radical explantation," J. Exp. Biol. 201:1203-1209 [1998].

Ihnken et al., "Studies of hypoxemic/reoxygenation injury: without aortic clamping," J. Thorac. Cardiovasc. Surg., 110:1182-1189 [1995].

Ihnken, "Hyperoxic cardiopulmonary bypass causes reoxygenation injury and lipid peroxidation," J. Thorac. Cardiovasc. Surg., 114:304-305 [1997].

Oldham and Bowen, "Oxidative stress in critical care: is antioxidant supplementation beneficial?" J. Am. Diet. Assoc. 98:1001-1008 [1998].

Novelli et al., "Vitamin E protects human skeletal muscle from damage during surgical ischemia-reperfusion," Am. J. Surg. 172:206-209 [1996].

* cited by examiner

CONTROLLED ENVIRONMENT DEVICE

This is a continuation of U.S. patent application Ser. No. 09/972,236, filed Oct. 5, 2001, now U.S. Pat. No. 6,685,622 B2 issued Feb. 3, 2004, which claims priority benefit to U.S. Provisional Patent Application No. 60/241,382, filed Oct. 17, 2000.

FIELD OF THE INVENTION

The present invention relates to devices and methods for providing controlled environments for surgical procedures, as well as transplantation and wound healing.

BACKGROUND OF THE INVENTION

Oxygen, a critical element in many biological systems, was independently discovered by Priestly and Sheele in 1774. Shortly thereafter, Lavoisier reported on the poisonous effects of oxygen inhalation and in 1878, Bert documented the poisonous effects of high oxygen tension levels on non-human animals (See, Knight, Ann. Clin. Lab. Sci., 28:331–346 [1998]). Experiments conducted as early as 1899 demonstrated that increased oxygen tension results in severe pulmonary congestion with pneumonia-like changes in mice, rats, and guinea pigs (See, Knight, supra). Indeed, in a 1909 medical text, it is indicated that " . . . there can be little doubt that the administration of oxygen may not be entirely harmless as stated in previous editions . . . " (as quoted by Knight, supra, at page 332). Thus, oxygen toxicity has long been recognized as a problem in physiological systems. However, the information regarding oxygen toxicity remained largely ignored by physicians for several decades. Significantly, the failure to recognize the potential toxic effects of increased oxygen tension resulted in an estimated 10,000 cases (worldwide) of blindness in newborns due to retrolental fibroplasia between the 1940s and 1950s (See, Knight, supra).

Final acceptance of the medical community that increased oxygen tension is potentially toxic to humans and other animals did not occur until a publication in 1967, which correlated the concentration and duration of inspired oxygen before death with pathologic lung findings at autopsy. The following year, the formation of pulmonary hyaline membranes in adults was associated with oxygen toxicity. In 1954, the hypothesis was presented that oxygen poisoning and X-irradiation have a common basis of action through the formation of oxidizing free radicals (See, Knight, supra). Nonetheless, it was not until the discovery of superoxide dismutase in 1969, that the presence of free radicals in biological systems was generally considered to be likely.

Today, the potential for damage caused by oxygen and oxygen radicals is well-recognized. Indeed, oxygen has been referred to as a "double-edged sword," (See, Knight, supra). Of course, oxygen is critical for most life forms, including humans. However, in order to benefit from the advantages provided by aerobic respiration, organisms have developed antioxidant enzymes and other means to detoxify reaction oxygen species and maintain essentially anaerobic conditions throughout all tissues, organs, and/or the vascular system. Without antioxidant enzymes (e.g., superoxide dismutases such as MnSOD and CuZnSOD), there is the possibility of damage to many biological molecules (e.g., DNA, RNA, proteins, and lipids). Accumulation of oxidatively damaged molecules leads to genetic mutations and cellular senescence. Indeed, any factors that compromise the activities of antioxidants may result in the accumulation of reactive oxygen species and the resultant damage caused by their action. It has also been suggested that decreasing antioxidant activities is associated with the aging process (See, Tian et al., Free Radical Biol. Med., 24:1477–1484 [1998]).

Oxygen therapy has been used for decades in various clinical settings. However, many essential intracellular reactions involving oxygen result in the formation of free radicals, and prolonged oxygen therapy is associated with a significant risk of toxicity. For example, exposure to pure oxygen leads to diffuse alveolar damage, with plasma exudation into the alveolar space. The subsequent death of endothelial and alveolar epithelial cells appear to be essential features of oxygen-induced alveolar damage, with the damaged cells exhibiting the effects of apoptosis (condensation and margination of chromatin) and necrosis (disruption of the plasma membrane) (Barazzone et al., Am. J. Resp. Cell Mol. Biol., 19:573–581 [1998]). Indeed, present recommendations indicate that humans should not be exposed to oxygen concentrations greater than 60% for prolonged time periods (See, Knight, supra).

In the surgical setting, oxygen toxicity is often observed in situations involving lung injury (e.g., postpneumonectomy pulmonary oedema [PPO]). PPO may be indistinguishable from severe acute respiratory distress syndrome (ARDS) or the less serious syndrome, acute lung injury (ALI). PPO is a significant operative concern, with reports indicating that PPO is a complication in 4–7% of pneumonectomies and 1–7% of lobectomies, and has an associated mortality rate of 50–100% (See, Williams et al., Eur. Respir. J., 11:1028–1034 [1998]). Ischemia-reperfusion injury has also been considered a contributor to PPO, related to lung damage caused by operative ischemia and injury caused by formation of reactive oxygen species during reperfusion. Despite improvements in therapies and management, the mortality rate in acute lung injury remains high. While these cases have involved injuries to lung tissues resulting from exposure to increased oxygen tensions, other organs and tissues have proven to be equally at risk from this type of exposure. In addition, problems associated with the formation of adhesions may be related to oxygen exposure of the tissues during surgery.

Oxidative myocardial injury due to oxygen-derived free radicals and nitric oxide has been shown to occur during hyperoxic (i.e., 300 to 400 mm Hg) cardiopulmonary bypass surgery. This has led to recommendations that reduced oxygen tension levels be utilized during cardiac operations (i.e., "normoxic" levels of about 140 mm Hg) (See, Ihnken et al., J. Thorac. Cardiovasc. Surg., 116:327–334 [1998]). This has been shown to be of particular importance in hypoxemic immature hearts (See, Morita et al., J. Thorac. Cardiovasc. Surg., 110:1235–1244 [1995]). Furthermore, reoxygenation of organs such as hearts may also cause injury (e.g., lipid peroxidation and functional depression) that may result in perioperative cardiac dysfunction (Ihnken et al., J. Thorac. Cardiovasc. Surg., 110:1171–1181 [1995]). In addition, cardiopulmonary bypass patients undergoing heart valve replacement surgery appear to be under oxidative stress, as compared with normal controls.

There are two additional episodes of oxidative stress that occur during bypass surgery (See, Pepper et al., Free Rad. Res., 21:377–385 [1994]). The first is produced when the patient is placed on extracorporeal blood circulation and oxygenation, which results in lipid peroxide and thiobarbituric acid-reactive substance increases. The second episode occurs during reperfusion of the myocardium following removal of the aortic cross clamp. This removal ends a period of ischemia and subjects the myocardium to reperfusion or reoxygenation injury. This injury is amplified by pro-oxidant biochemical changes resulting from extracorporeal oxygenation and blood circulation, as well as the effects of hemodilution.

In the central nervous system, oxidative injury can result in tremendous damage. For example, oxidative stress has been associated with such severe syndromes as Parkinson's disease and Alzheimer's disease and familial amyotrophic lateral sclerosis (ALS) (See, Satoh et al, Cell. Mol. Neurobiol., 18:649–666 [1998]).

The situation is similar in the transplantation setting. For example, during long-term in vitro preservation and reperfusion of hearts for transplantation, irreversible tissue damage occurs due to reactive oxygen species. Thus, efforts have been made to inhibit the generation of oxygen-derived free radicals and the associated oxidative damage of ischemic tissue through the use of cold conditions and specially formulated buffer solutions (See, Sellke et al., J. Surg. Res., 80:171–176 [1998]; Cargnoni et al., J. Heart Lung Transplant., 18:478–487 [1999]). Nonetheless, the time limits for donor organ transport remain limited to several hours.

Thus, it is clear that what is needed are improved methods and devices that reduce the potential for oxidative injury during surgical procedures, as well in the transport of samples, organs/tissues, etc. It is also clear that improved methods are needed which allow the operator (i.e., surgeon) to carefully control and monitor the gases in the theater surrounding a surgical field as appropriate for the surgical procedure.

SUMMARY OF THE INVENTION

The present invention relates to devices and methods for providing controlled environments for surgical procedures, as well as transplantation and wound healing. In particular, one embodiment of the present invention provides devices and methods to provide an anaerobic environment for incision sites. In other embodiments, the present invention provides devices and methods to maintain anaerobic conditions during the collection, transport, and implantation of organs, tissues, cells, and other transplant material. In further embodiments, the present invention provides devices and methods for the production and maintenance of an anaerobic environment surrounding sites of trauma or tissue injury. In particular, the present invention provides devices and methods which allow the operator to strictly control the environment for surgical procedures, transplantation and wound healing, etc. Thus, the present invention also finds use in specialized settings where hyperoxic conditions are desirable.

The present invention provides devices for maintaining a surgical field in an isolated environment comprising an enclosure for separating a surgical field from an atmosphere ambient to the device, and at least one access port, wherein the access port enables admission into the enclosure. In one embodiment, the at least one access port enables admission of at least one surgical means into the enclosure. In another embodiment, the surgical means is selected from the group consisting of surgical instruments, robotics, sensors, and human hands. In another embodiment, the devices of the present invention comprise means for evacuating the isolated environment. In one particularly preferred embodiment, the evacuating produces an environment with reduced oxygen tension. In an alterative preferred embodiment, the reduced oxygen tension within the device is essentially oxygen-free. In yet another embodiment, the devices of the present invention further comprise means for refilling the isolated environment. In one preferred embodiment, the refilling produces an environment with reduced oxygen tension, while in another preferred embodiment, the reduced oxygen tension is essentially oxygen-free. In an alternative embodiment, the refilling produces an environment with an increased oxygen tension. In yet an additional embodiment, the devices of the present invention further comprise means for filling the isolated environment, while in alternative embodiments, the filling produces an environment with reduced oxygen tension. In some preferred embodiments, the filling produces an environment with an increased oxygen tension. In other particularly preferred embodiments, the isolated environment is essentially pathogen-free. In still other preferred embodiments, the devices of the present invention further comprise a transport attachment. In some particularly preferred embodiments, the transport attachment is lockingly engaged to the device, while in other particularly preferred embodiments, the transport attachment is detachably engaged to the device. In still further particularly preferred embodiments, the transport attachment has a reduced oxygen tension.

The present invention also provides devices for maintaining an injured area in an isolated environment comprising an enclosure for separating an injured area from the atmosphere ambient to the device, wherein the oxygen tension of the isolated environment is controllable. In some embodiments, the devices comprise at least one access port. In alternative embodiments, the devices further comprise means for evacuating the isolated environment. In still other embodiments, the evacuating comprises means for oxygen release and retention of a heavy gas within the isolated environment. In some particularly preferred embodiments, the evacuating produces an environment with reduced oxygen tension, while in other particularly preferred embodiments, the reduced oxygen tension is essentially oxygen-free. In additional embodiments, the devices further comprise means for refilling the isolated environment. In one preferred embodiment, the refilling produces an environment with reduced oxygen tension, while in another preferred embodiment, the reduced oxygen tension is essentially oxygen-free. In an alternative embodiment, the refilling produces an environment with an increased oxygen tension. In yet an additional embodiment, the devices of the present invention further comprise means for filling the isolated environment, while in alternative embodiments, the filling produces an environment with reduced oxygen tension. In some preferred embodiments, the filling produces an environment with an increased oxygen tension. In other particularly preferred embodiments, the isolated environment is essentially pathogen-free. In still other preferred embodiments, the devices of the present invention further comprise a transport attachment. In some particularly preferred embodiments, the transport attachment is lockingly engaged to the device, while in other particularly preferred embodiments, the transport attachment is detachably engaged to the device. In still further particularly preferred embodiments, the transport attachment has a reduced oxygen tension. In other particularly preferred embodiments, the injured area is selected from the group consisting of surgical incisions, burns, lesions, and broken bones.

The present invention also provides means for maintaining material (i.e., material of interest) in an isolated environment comprising an enclosure for separating the material from an atmosphere ambient to the device, wherein the oxygen tension of the isolated environment is controllable. In one preferred embodiment, the devices comprise at least one access port. In another preferred embodiment, the devices further comprise means for evacuating the isolated environment. In still other embodiments, the evacuating comprises means for oxygen release and retention of a heavy gas within the isolated environment. In some particularly preferred embodiments, the evacuating produces an environment with reduced oxygen tension, while in other particularly preferred embodiments, the reduced oxygen tension is essentially oxygen-free. In additional embodiments, the devices further comprise means for refilling the isolated environment. In one preferred embodiment, the refilling produces an environment with reduced oxygen tension, while in another preferred embodiment, the reduced oxygen tension is essentially oxygen-free. In an alternative embodiment, the refilling produces an environment with an increased oxygen tension. In yet an additional embodiment, the devices of the present invention further comprise means for filling the isolated environment, while in alternative embodiments, the filling produces an environment with reduced oxygen tension. In some preferred embodiments, the filling produces an environment with an increased oxygen tension. In other particularly preferred embodiments, the isolated environment is essentially pathogen-free. In still other preferred embodiments, the devices of the present invention further comprise a transport attachment. In some particularly preferred embodiments, the transport attachment is lockingly engaged to the device, while in other particularly preferred embodiments, the transport attachment is detachably engaged to the device. In still further particularly preferred embodiments, the transport attachment has a reduced oxygen tension. In yet other particularly preferred embodiments, the material is transplant material. In still other particularly preferred embodiments, the transplant material is selected from the group consisting of organs, tissues, cells, and artificial materials. In an additional embodiment, the maintaining comprises transporting the material.

DESCRIPTION OF THE INVENTION

The present invention relates to devices and methods for providing controlled environments for surgical procedures, as well as transplantation and wound healing. In particular, one embodiment of the present invention provides devices and methods to provide an anaerobic environment for incision sites. In other embodiments, the present invention provides devices and methods to maintain anaerobic conditions during the collection, transport, and implantation of organs, tissues, cells, and other transplant material. In further embodiments, the present invention provides devices and methods for the production and maintenance of an anaerobic environment surrounding sites of trauma or tissue injury. In particular, the present invention provides devices and methods which allow the operator to strictly control the environment for surgical procedures, transplantation and wound healing, etc. Thus, the present invention also finds use in specialized settings where hyperoxic conditions are desirable.

In particularly preferred embodiments, the present invention provides methods and devices to protect the interior of the body from diatomic oxygen (i.e., $O_2$) or superoxygen radicals (e.g., superoxide $O_2^-$) during surgery, as well as during harvesting and/or implantation of organs or cells. Thus, the present invention helps prevent the injury associated with oxygen toxicity to vital organs (e.g., heart, lungs, and central nervous system).

In one embodiment, the devices of the present invention provide a controlled surgery environment that surrounds the surgical field from the time prior to the actual surgery to after the conclusion of surgery. Importantly, the present invention allows ready access to the surgical field by the surgeon, nurses, and others involved in the procedure, as well as allowing insertion of instruments, monitoring instruments, devices, sampling materials (e.g., for microbiological cultures, biopsies, etc.), implantable devices (e.g., pacemakers, bone pins, hearing devices, etc.), and donor tissues/organs without compromising the integrity of the surgical field. In some embodiments, the present invention provides a controlled environment for surgical procedures such as Caesarian sections. In these embodiments, the device used is larger than many other embodiments in order to accomodate the size of the mother's abdomen and allow sufficient room for the surgical team to work. In addition, in some cases, the incision area will be quite large. Thus, the actual surface of the adhesive in contact with the mother's skin may be relatively small. In preferred embodiments, there is an airlock and/or transport device docked with the controlled surgical environment. The airlock and/or transport device are used to remove the baby from the controlled surgical environment. When the transport device is used, it can be charged with a gas mixture that is appropriate for the baby.

In certain preferred embodiments, the maintenance of an anaerobic environment around the surgical incision or trauma site prevents the introduction or exposure of oxygen into the tissues or organs, as well as preventing microbial contamination of the site. Indeed, the present invention provides an aseptic, oxygen-controlled surgical "theater" for the performance of surgeries.

It is not intended that the present invention be limited to situations in which a reduced oxygen tension or essentially anaerobic environment is desirable. Indeed, it the present invention provides advantages in cases where it is necessary or desireable for the environment surrounding a surgical field be strictly controlled. For example, it is contemplated that the present invention will find use in cases (e.g., certain surgeries) where hyperoxic conditions are desireable. In addition, it is contemplated that the present invention will find use in cases where modified concentrations of other gases are desireable. For example, it is contemplated that the present invention will be used in cases where increased or decreased nitrogen concentrations are favored. In sum, the present invention provides the means to control the environment surrounding a surgical area (i.e., the "surgical theater").

It is not intended that the present invention be limited to any particular size or configuration. Indeed, the shape and size of the device is largely dependent upon the particular procedure to be performed using the device or the particular reason for using the device. For example, in some cases, a larger dome is needed, while in others a smaller dome is preferred. In addition to the dome size, other design considerations are contemplated. Thus, any shape, size, or configuration of the present invention is contemplated, so long as the environment within the device is controllable and/or optimal for the procedure being conducted or the particular reason for using the device.

Furthermore, although preferred embodiments of the present invention involve human patients, it is not intended that the present invention be limited to use with humans. Indeed, it is contemplated that the present invention will find use in the veterinary setting as well as the clinical setting. In addition, it is contemplated that the present invention will find use both in established surgical centers as well as in the field.

Controlled Surgery Environment (CSE)

Figure 1:
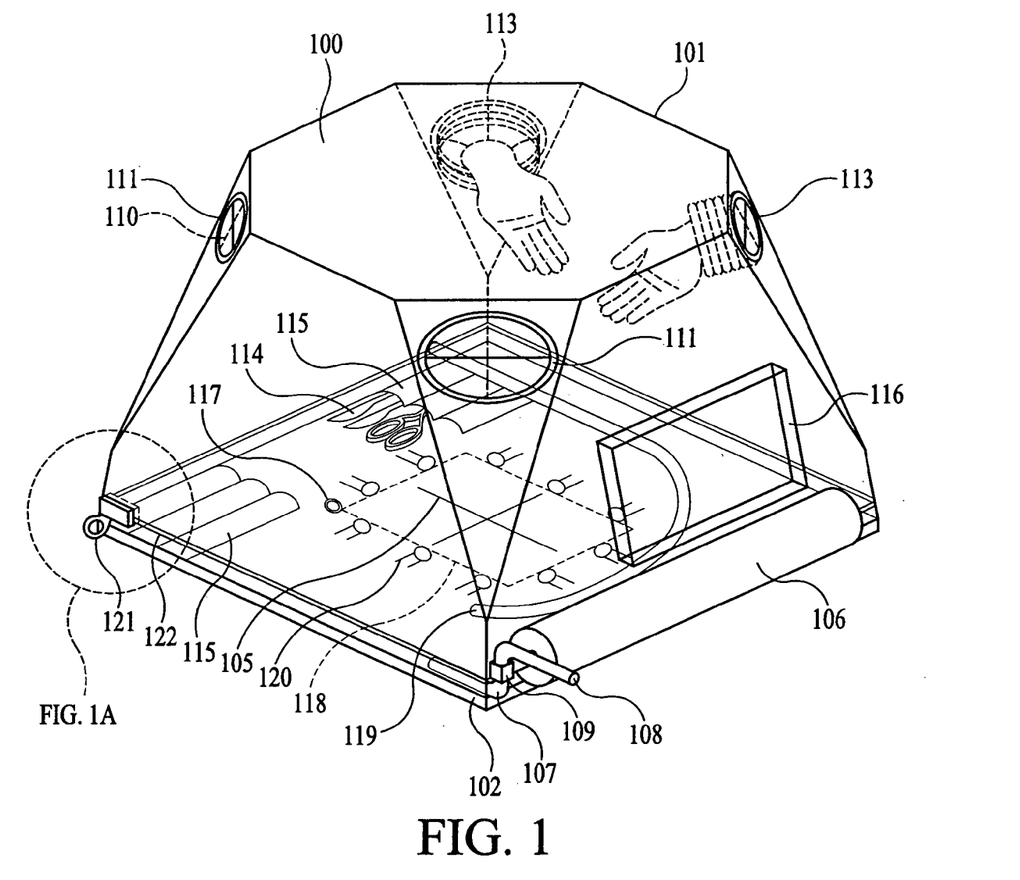
FIG. 1 is an overall perspective view of one embodiment of the controlled environment device of the present invention. In particular, this Figure provides an overall perspective view of one embodiment of a controlled surgical environment of the present invention, FIG. 1A provides an enlarged cross-sectional view of the base pad portion of the controlled environment device shown in FIG. 1.

In one preferred embodiment of the invention, as illustrated in FIG. 1, the controlled surgery environment (CSE) (100) comprises an inflatable, flexible transparent plastic dome (101). This surgery dome can be easily collapsed into a flat package for storage prior to use and for disposal. Indeed, it is contemplated that the devices of the present invention will find use as disposable (i.e., one use) CSEs. However, it is contemplated that the devices will be decontaminated following use and reused as needed or desired. In addition, it is not intended that the present invention be limited to an embodiment in which the CSE is collapsed (i.e., evacuated) prior to its use. Thus, in some embodiments, the CSE is evacuated of any gas within the dome and then filled with the desired gas prior to the beginning of surgery.

Figure 1A:
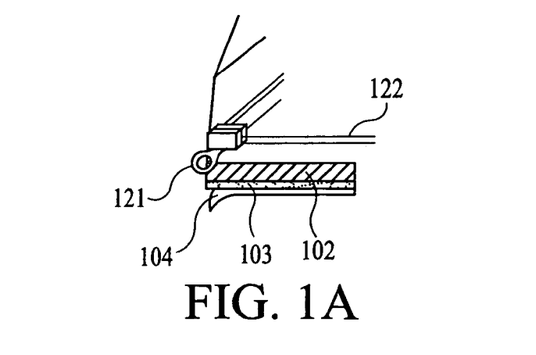

A pad (102) on the package has a sterile adhesive (103) with a backing (104) that can be removed to expose the sterile adhesive (103). In preferred embodiments, the collapsed (i.e., evacuated) pad is positioned over the surgical field such that the surgery grooves (105) are in alignment with marks drawn on the patient's skin during surgical preparation to delineate the surgical field. Prior to beginning the surgical procedure itself, the backing (104) is removed and the pad (102) is pressed on to the patient such that the adhesive (103) securely binds to the patient's skin in the proper orientation.

Sterile, gas (e.g., nitrogen, argon, or other suitable gases) supplied by an attached compressed gas cylinder (106) or via an inlet for another source (108), is introduced into the CSE by means of a gas supply inlet (107) to inflate the surgery dome (101). A gas pressure valve and regulator (109) mounted on the CSE is used to control the amount of gas introduced into the CSE and to maintain a positive pressure on the dome, thereby preventing unwanted gas (e.g., oxygen) and microorganisms from entering into the surgical theater. By placing the CSE over the surgical field and filling it with nitrogen (or another suitable gas or combination of gases) prior to exposing the internal organs to the environment, the risk of oxygen toxicity and microbial contamination are greatly reduced. Thus, in some particularly preferred embodiments, the present invention prevents the contamination of the surgical field by oxygen and microorganisms from the time that the body's internal organs are exposed until after the incision is closed.

Surgical personnel insert their hands into the CSE by either inserting their pre-gloved hands through an elastic iris membrane (110) in the appropriate access ports (111), or into gloves (112) that are an integral part of the dome (101). In addition to the surgeon's access ports, in preferred embodiments, there are ports (113) available for surgical assistants (e.g., nurses, additional surgeons, assistants, etc.). As with the surgeon's access ports, these ports may also be fitted with gloves (not shown). In particularly preferred embodiments, the iris membranes collapse to seal off the dome when it is not in use and compress tightly around a gloved arm placed inside the CSE. However, it is not intended that the present invention be limited to access by human hands. For example, it is contemplated that mechanical devices, including but not limited to robots, fiber optics, and lasers will be used in conjunction with the present invention. In some embodiments, entry of these mechanical devices into the interior of the CSE is achieved through any of the access ports present in the invention. In other embodiments, access is achieved through ports that are specially tailored to the device.

In some embodiments, once the personnel's hands are inside the dome (101), the appropriate surgical instrument(s) (114) may be selected from an integral instrument storage area (115) inside the dome. In alternative embodiments, the instruments are received through an airlock (116) positioned on the side of the dome. In some embodiments, the airlock is an iris self-sealing membrane that conforms to the instruments as they are passed into the dome. In other embodiments, the airlock mechanically attaches to an external controlled transport environment (CTE).

Figure 2:
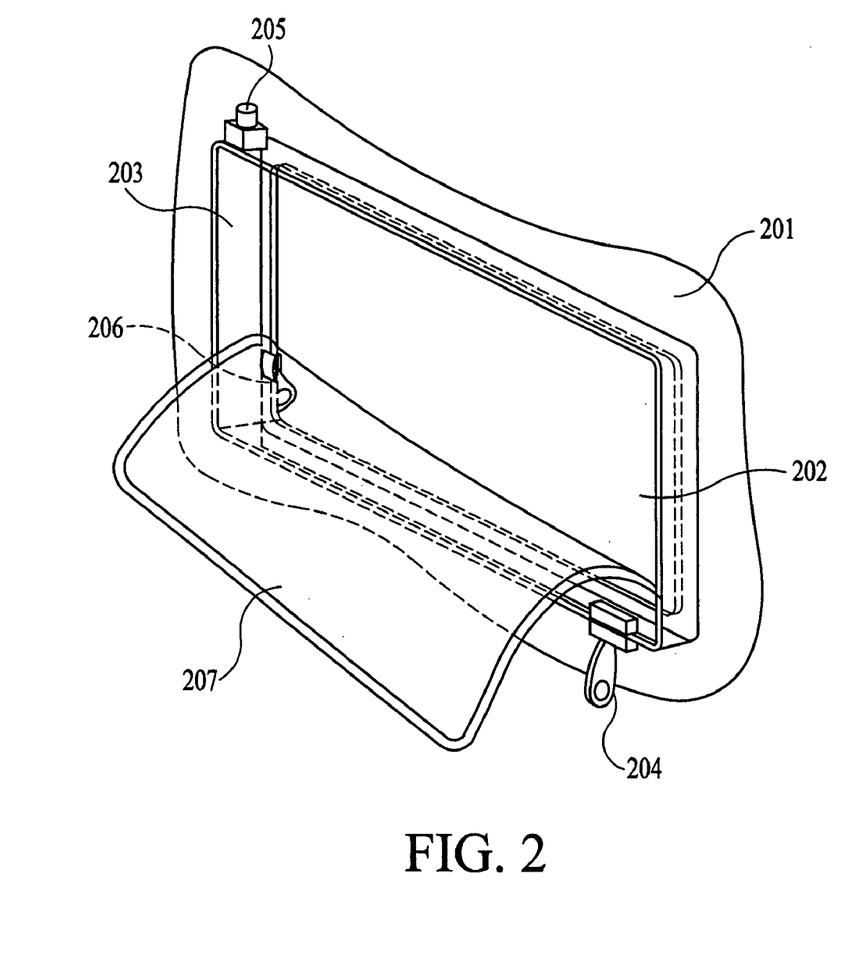
FIG. 2 is an enlarged perspective view of the airlock of one embodiment of the controlled environment device of the present invention.

A preferred embodiment of an airlock of the present invention is provided in FIG. 2. In this Figure, the wall of the CSE (201) which leads into the interior (202) of the CSE is shown. The airlock mating baffle (203) is indicated, as is the airlock mating zipper (204), airlock evacuation nozzle and cut-off valve (205), CSE access zipper (206), and CSE access port (207).

Surgical instruments, tissues, organs, and/or other needed supplies or equipment are placed inside the CTE prior to the beginning of surgery. In some preferred embodiments, the CTE is attached to the CSE prior to the expulsion of air and the introduction of inert sterile gas. Thus, in these embodiments, the CTE is also evacuated at the same time as the CSE. As with instruments, tissues for grafting and organs for transplantation may also be passed through the airlock (116; as shown in FIG. 1) or placed within a storage area (not shown) within the dome prior to the beginning of the surgical procedure.

In some embodiments, once ready to begin the actual operation, the surgeon or other personnel pulls the surgical area pull tab in the base pad (117) to draw the surgical area pull wire (118) into a pre-defined pattern, thereby exposing the surgical field on the patient's body to the controlled surgery environment and provide the surgeon access to the incision site.

During the operation, blood and other liquids are removed from the surgical field by a suction hose (119) connected to an external suction pump. Clamps and other surgery fixtures may be attached as needed, to the base pad by means of retractor anchors (120). These fixtures are connected to the dome in a manner such that the integrity of the controlled environment is not compromised.

In another embodiment, the surgeon (or another member of the surgery team) makes at least one incision directly through the base pad. In this embodiment, only the interior of the body is exposed to the atmosphere of the CSE. No exterior portions of the body (e.g., the skin) are exposed to the interior of the CSE, thereby further reducing the potential for contamination of the incision(s) or internal organs by the patient's skin flora.

In cases of unexpected complications during the surgical procedure, the present invention is designed so that the surgeon or other personnel can quickly remove the dome from the patient. This allows the access of additional personnel to the surgical field, as well as the use of equipment that does not fit within the confines of the dome. In such cases, the surgeon or other personnel pulls the emergency access zipper tab (121) along the emergency access pull zipper seam (122), which separates the dome from its base. Although this destroys the integrity of the surgical field as the internal organs are exposed to ambient air, this may be required in some cases.

The present invention is not limited to any particular material or embodiment. Indeed, the CSE and CTE can be made out of any suitable material. For example, although plastics are lighter and perhaps easier to work with, it is intended that materials such as plexiglass and other materials will be useful in the present invention. Indeed, it is intended that flexible materials as well as rigid materials will find use in the present invention. Also, in other embodiments, the surgeon, other personnel, and/or mechanical devices are provided access to the surgical field by means of ports positioned on the top of the CSE. In such embodiments, a controlled environment can be created by providing a high flow of sterile nitrogen (or other appropriate gas) inside the walls of the CSE, thereby preventing unwanted gas (e.g., oxygen) from coming into contact with the patient's internal organs or the surgical field.

In alternative embodiments, the gas utilized in conjunction with the present invention provides an increased oxygen concentration, as compared to the ambient environment. Although it is recognized that anaerobic conditions are typically preferred for surgical methods in which internal organs are exposed to the ambient environment, it is contemplated that in certain settings involving skin and other externally located organs, hyperoxic conditions are preferred. Thus, the present invention provides the means to produce such conditions in a highly controllable manner. In addition, the conditions can be adjusted as the device is being used, thereby optimizing the gas concentration and composition for each stage of a surgical procedure. Thus, the patient receives the most appropriate gas concentration and composition for the particular surgery and patient involved.

In addition, it is contemplated that the CSE integrity may be maintained after completion of surgery. For example, in some embodiments the CSE is maintained through the post-operative period and/or through some or all of the recovery period. Thus, it is possible to maintain the controlled environment surrounding a surgical incision for the optimum amount of time to speed proper healing.

Controlled Transport Environment (CTE)

The present invention also provides a controlled transport environment (CTE) suitable for the storage and transport of organs, tissues and cells. In particular, this embodiment is suited for use with organs and tissues for transplantation. For example, organs harvested from a donor and placed within an CTE are maintained in the CTE until transplanted in a recipient. In particularly preferred embodiments, the organs are harvested and transplanted using the CSE of the present invention under anaerobic conditions, with the CTE docked to the CSE (i.e., via the airlock, for example, as shown in FIG. 2). In this manner, the organs are never exposed to atmospheric oxygen and the chances for oxidative injury are greatly reduced. In addition, the chances of microbial contamination of the organs and transplant site are minimized.

The removal, preparation and transport of organs and tissues remains an extremely problematic aspect of transplant surgery, particularly for organs such lungs, livers, and hearts. As briefly discussed above, the removal of organs from their normal, anaerobic environment within the body and exposure to oxygen results in oxidative damage to these organs. Indeed, the damage can be sufficient to render the organs unusable for transplantation purposes. The same considerations are involved in the harvesting, transportation and implantation of graft tissues and cells.

The CTE of the present invention provides a complete, self-contained controlled environment for the transport of tissues and organs between a donor and recipient. In particularly preferred embodiments, the CTE is docked via the airlock to the CSE in which the donor organs/tissues are removed, and the organs/tissues placed within the CTE under anaerobic conditions. The CTE is then sealed and transported to the site of the transplantation to the recipient. The CTE containing the organs/tissues is then docked to the CSE in which the recipient is to undergo surgery under anaerobic conditions. The organs/tissue are then removed from the CTE and implanted into the recipient. In this manner, the use of the CSEs and CTE maintains the organs/tissues in a sterile anaerobic environment. In addition, the use of the CTE allows the organs/tissues to enter the CSE while maintaining the integrity of the CSE.

Figure 3:
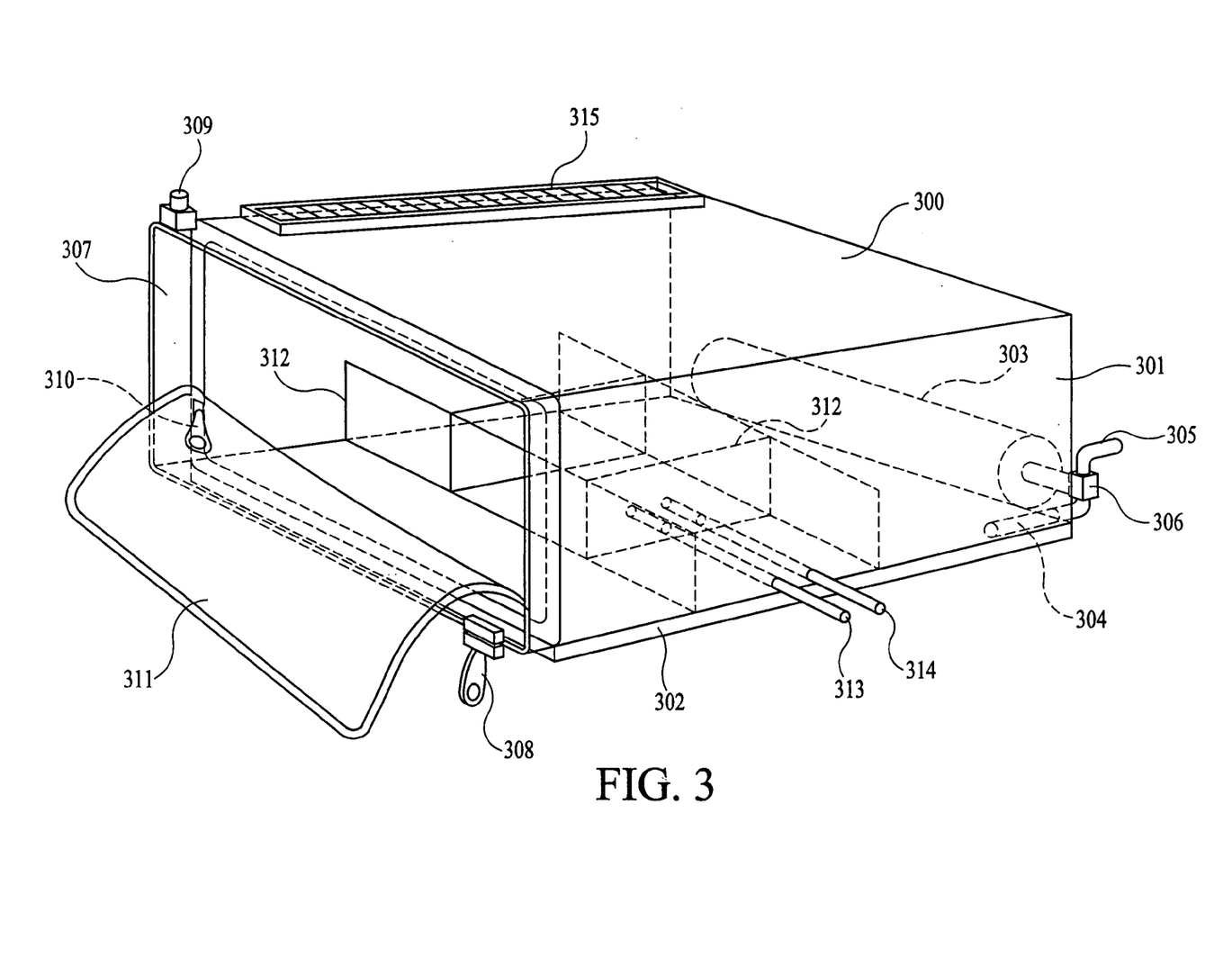
FIG. 3 is an overall perspective view of one embodiment of the controlled environment transport device of the present invention. In particular, this Figure provides an overall perspective view of one controlled environment transport device of the present invention.

FIG. 3 provides a schematic of a preferred embodiment of the CTE of the present invention. The CTE (300) has an inflatable, flexible plastic dome (301) attached to a semi-rigid base pad (302). In some preferred embodiments, the plastic of the dome (301) is transparent, although in alternative embodiments, the plastic is translucent or opaque. The CTE is initially collapsed (i.e., with no air present in its interior) prior to use. Sterile, gas (e.g., nitrogen, argon, other suitable gas, and/or mixture of gases) supplied by an attached compressed gas cylinder (303) or via an inlet for another source (305), is introduced into the CSE by means of a gas supply inlet (304) to inflate the surgery dome (301). A gas pressure valve and regulator (306) mounted on the CSE is used to moderate the amount of gas introduced into the CSE. The valve and regulator (306) serve to maintain a positive pressure on the dome, thereby preventing unwanted gas (e.g., oxygen) and microorganisms from entering into the surgical theater. In one embodiment, the valve and regulator functions to cut off the gas supply after inflation, sealing the gas inside the CTE. This allows the transport of the CTE without an attached gas cylinder or external gas supply.

At an appropriate time during surgery to remove a donor organ or tissue, the CTE is attached to an CSE by aligning its airlock mating baffle (307) with the CSE's airlock mating baffle (shown as (203) in FIG. 2), and engaging the CTE's airlock mating zipper (308) to seal the baffles together. This creates an airtight airlock between the CSE and CTE. A vacuum hose is then attached to the airlock evacuation nozzle and valve (309) and the air within the airlock is removed, thereby collapsing it. Then, a gas supply hose is attached to the airlock evacuation nozzle and valve and the airlock is inflated with sterile gas (e.g., anaerobic gas).

At this point, the access port on the CSE side of the airlock (shown as (207) in FIG. 2) is opened and the surgeon or assistant reaches into the airlock to the CTE access port zipper (310). Operating the zipper (310) opens the CTE access port (311) to fully connect the CTE and CSE. The organ(s) and/or tissue(s) are transferred from the donor into the appropriate cavities formed by the organ/tissue containment baffles (312) of the CTE. The blood/blood substitute delivery hose (313) and blood/blood substitute removal hose (314) may then be attached to appropriate arteries and/or veins in the harvested organs, if desired that the organ be supplied with cooled fluid during transport. In some embodiments, the fluid is oxygenated blood (e.g., normoxic blood), while in other embodiments, a blood substitute is used. Finally, the airlock unsealing process is reversed, first to seal the CTE and then to seal the CSE, and finally to detach the CTE from the CSE. The CTE is then transported to the site of the transplant operation, where it is docked to the CSE used in the transplant operation. Docking is accomplished using the same procedures as described for harvesting the organ(s)/tissue(s). The organ(s)/tissue(s) are removed from the CTE and the transplant operation is completed. During all phases of this process, the oxygen trap/exhaust (315) is used to either trap and hold or exhaust any trace oxygen that has remained in the CTE or its airlock from the initial filling and airlock mating, or that has outgassed from the inside surface of the CTE.

The CTE is also suited for use as a container to anaerobically condition and then transport surgical instruments, fixtures, devices, sensors, pacemakers, other implantable devices, etc., into an CSE via the airlock. In addition, it is contemplated that the CTE of the present invention will find use alone as a device to transport organs, tissues and cells, without the use of the CSE. In these cases, the instruments, devices, organs, tissues, cells, etc., are placed in the CTE under usual aerobic conditions and the CTE is evacuated via its gas supply inlet (304) and valve (306), and then filled with sterile gas (e.g., anaerobic gas). Pre-packaged surgery instruments may also be stored in an evacuated condition (e.g., anaerobically) in CTEs and the CTEs inflated as needed.

Controlled Environment Trauma Bandage (CETB)

The present invention also provides a controlled environment trauma bandage (CETB) suitable to produce and maintain a controlled environment over a trauma site. As shown in the preferred embodiment illustrated in FIG. 4, this embodiment is similar to the CSE in that the bandage provides a controlled environment that can be positioned over the site of an injury or incision. The CETB (400) comprises an inflatable, flexible transparent plastic dome (401). This dome can be easily collapsed into a flat package for storage prior to use and for disposal. Indeed, it is contemplated that the devices of the present invention will find use as disposable (i.e., one use) CETBs. However, it is contemplated that the devices will be decontaminated following use and reused as needed or desired. A pad (402) on the package has a sterile adhesive (403) with a removable backing (404) that can be removed to expose the sterile adhesive (403). The pad is positioned over the trauma site, such that the site is covered by the dome of the CETB, and the pad (402) is pressed on to the patient such that the adhesive backing (403) securely binds to the patient's skin in the proper orientation.

Figure 4:
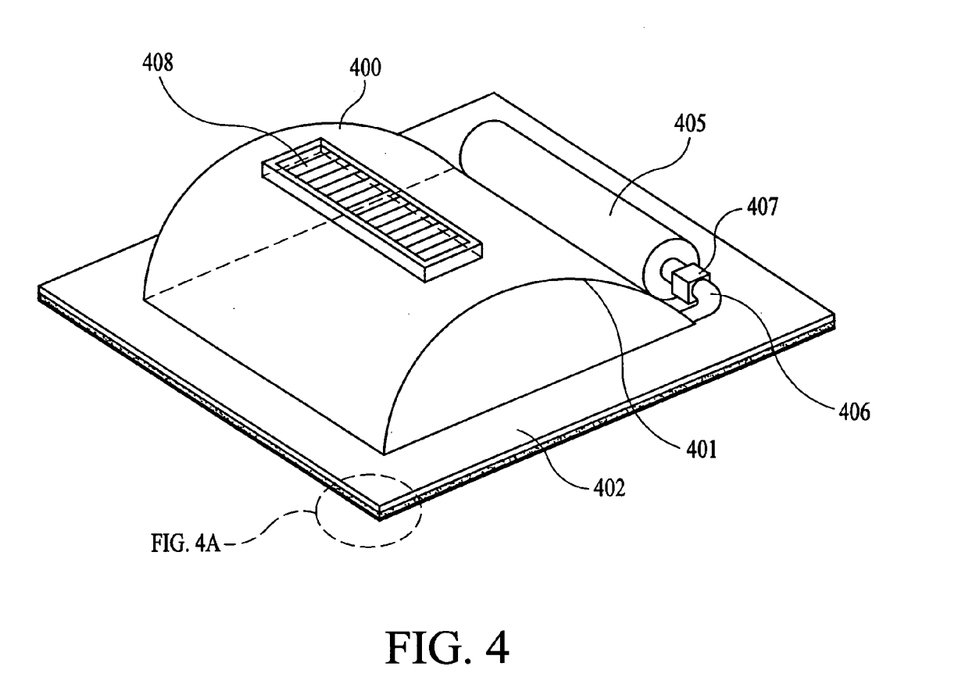
FIG. 4 is an overall perspective view of one embodiment of the controlled environment device of the present invention. In particular, this Figure provides an overall perspective view of one controlled environment trauma bandage embodiment of the present invention.
Figure 4A:
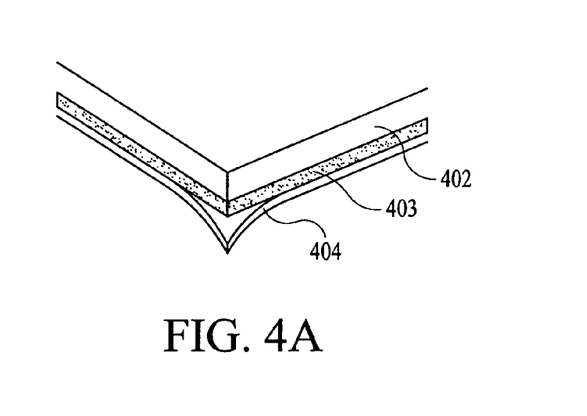
FIG. 4A provides an enlarged cross-sectional view of the base pad of the controlled environment device shown in FIG. 4.

Sterile, anaerobic gas (e.g., nitrogen, argon, or another desired gas) supplied by an attached compressed gas cylinder (405) or via an inlet for another external source (not shown), is introduced into the CETB by means of a gas supply inlet (406) to inflate the CETB dome (401). A gas pressure valve and regulator (407) mounted on the CSE are used to moderate the amount of gas introduced into the CETB. The valve and regulator (407) serve to maintain a positive pressure on the dome, thereby preventing unwanted gas (e.g., oxygen) and microorganisms from entering into CETB. In some embodiments, the collector (408) traps oxygen, while in other embodiments the collector (408) preferentially allows the escape of oxygen out of the dome, while restricting or preventing the escape of a heavy gas (e.g., nitrogen). Thus, the present invention prevents the contamination of the trauma site. As with the CSE, the CETB is not limited to any particular material or embodiment. Indeed, the CETB can be made out of any suitable material.

Definitions

As used herein, the term "anaerobic" refers the absence of oxygen, while the term "aerobic" refers to the presence of oxygen. As used herein, the term "essentially anaerobic" refers to environments in which there is minimally detectable oxygen.

As used herein, the term "altered oxygen tension" refers to an environment in which the oxygen tension is different from that of the ambient atmosphere. In particularly preferred embodiments, the oxygen tension is less than that of the ambient atmosphere.

As used herein, the term "reduced oxygen tension" refers to an environment in which the oxygen tension is less than that of the ambient atmosphere. In some embodiments, the term refers to $E_h$ (i.e., oxidation-reduction potential) values less than 125 mv, while in other embodiments, the term refers to $E_h$ values of –150 to –250 mv, while in other embodiments, the term refers to $E_h$ values of less than –250 mv. In other embodiments, the term refers to reduced oxygen concentrations. For example, in preferred embodiments, the oxygen concentration of the isolated environment is less than 20 parts per million of dissolved oxygen. However, it is not intended that the present invention be limited to any particular oxygen concentration.

As used herein, the term "increased oxygen tension" refers to an environment in which the oxygen tension is greater than that of the ambient atmosphere. In some embodiments, the term refers to $E_h$ values greater than 250 mv.

As used herein, the term "oxygen-free" refers to the absence of detectable oxygen.

As used herein, the term "hyperoxia" refers to an excess of oxygen in the system of interest (e.g., tissue, an organ or body), while the term "hypoxia" refers to a decreased concentration of oxygen in the system of interest. While used to describe an isolated environment, the term hyperoxia refers to an oxygen concentration that is greater than that of the ambient atmosphere (i.e., outside of the isolated environment), wihle hypoxia refers to an oxygen concentration that is less than that of the ambient atmosphere (i.e., outside of the isolated environment).

As used herein, the term "normoxic" refers to an oxygen concentration that is normal for the tissue and/or organ of interest. In some cases, normoxic conditions are those in which no oxygen is present (e.g., deep internal organs), while in other situations, the term encompasses relatively high oxygen concentrations (e.g., the skin or eye surfaces). Thus, it is intended that the term encompass the normal oxygen concentration for the location or site of interest. When used to describe an isolated environment, the term refers to an oxygen concentration that is the same as that of the ambient atmosphere (i.e., outside of the isolated environment), such as the oxygen concentration under standard conditions.

As used herein, the term "hypernitric" refers to a nitrogen concentration that is greater than of the ambient atmosphere, while the term "hyponitric" refers to a nitrogen concentration that is less than that of the ambient atmosphere. In preferred hyponitric environments, nitrogen is minimally detectable. As with oxygen, the terms may also be used in reference to the amount of nitrogen present in an in vivo system or in a cell, organ, tissue, etc.

As used herein, the term "controlled environment" refers to an environment that is regulated by an operator, so as to provide the desired environmental conditions within a controlled environment device. Thus, it is intended that the term encompass environments within controlled environment devices that are optimum for surgical procedures (e.g., CSEs), transport of specimens, transplant materials, etc. (e.g., CTEs), and healing (e.g., CETBs).

As used herein, the terms "radical" and "free radical" refer to atoms, molecules, or compounds that contain an unpaired electron. The terms encompass, but are not limited to oxygen radicals (e.g., oxyradicals).

As used herein, the term "oxidative stress" refers to conditions in which oxidation presents a threat to biological or other systems, including but not limited to cells, tissues, organs, etc. For example, under such conditions, the presence of oxygen has detrimental effects on the structure, function, and/or physiology of the biological system involved. In addition, the term encompasses the detrimental effects of oxygen on inanimate objects.

As used herein, the term "surgical theater" refers to the space directly surrounding and in close proximity to the surgical field. Thus, surgical personnel operate within the surgical theater. In preferred embodiments, the term encompasses the surgical field and surrounding space. In particularly preferred embodiments, the surrounding space encompasses the interior of a CSE, CTE or CTEB.

As used herein, the term "surgical field" refers to the area in which surgical personnel are conducting a surgical procedure. It is intended that the term encompass the incision site as well as any internal areas within the surgical patient that are exposed to the outside environment due to the incision.

As used herein, the term "surgery" refers to any medical intervention that involves cutting or tearing the skin or other organs. In many cases, the cutting or tearing results in the exposure of internal organs and/or tissues to the environment. It is not intended that the term be limited to any particular type of surgical procedure. Indeed, it is intended that the term encompass microscopically-aided surgery (e.g., arthroscopic surgery), as well as stereotactic and other surgical methods.

As used herein, the term "surgical means" refers to any item that can be used to perform or assist with surgery. It is intended that the term encompass human hands, as well as surgical instruments, lasers, robotics, remote-controlled surgical instruments, microprocessor-controlled instruments, sensors (e.g., electronic and other equipment used to assist the surgical team in assessing the status of the patient), monitors (e.g., monitors for vital function measurements, etc.), etc. Thus, it is not intended that the present invention be limited to any particular means for performing or assisting surgery.

As used herein, the term "transplantation" refers to the transfer of an organ and/or tissue from one human or non-human animal (i.e., a "donor") to another human or non-human animal (i.e., a recipient). It is not intended that the donor and/or recipient be limited to humans. Indeed, it is intended that the donor and/or recipient be of any species. In addition, the term encompasses the introduction of synthetic or materials prepared in vitro, for use in transplantation. For example, the term encompasses the use of synthetic or artificial substances (e.g., bone and skin). In addition, the term encompasses the introduction of artificial devices or prosthetics (e.g., heart valves, stents, joints, monitors, pacemakers, etc.). The term "transplant" refers to the material (organ, tissue, cells, artificial substances, devices, etc.) to be transplanted.

As used herein, the term "graft" refers to a portion of tissue or a collection of cells that is suitable for implantation or transplantation. It is intended that the term encompass any graft material and types, including but not limited to autologous, avascular, accordion, autodermic, autoepidermic, bone, fascicular, full-thickness, heterologous, heteroplastic, xenografts, nerve, muscle, tendon, ligament, synthetic, and other suitable grafts, including grafts obtained from biological material grown in vitro. The term "grafting" refers to the process of implanting or transplanting a graft.

As used herein, the term "ischemia" refers to a deficiency of blood in a part, often due to functional or actual constriction or obstruction of a blood vessel.

As used herein, the term "perfusion" refers to the passage of liquid over and/or through an organ, while the term "reperfusion" refers to the passage of liquid over an/or through an organ which was previously unperfused (e.g., an artery clamped during surgery to prevent passage of blood).

As used herein, the term "isolated environment" refers to an environment that is separated from the ambient atmosphere by means of an enclosure. In particularly preferred embodiments, the isolated environment of the present invention has a reduced oxygen tension and is essentially pathogen-free.

As used herein, the term "pathogen-free" refers to the absence of pathogenic organisms, including, but not limited to bacteria, viruses, prions, fungi, and parasites.

As used herein, the term "flexible" refers to an item that is pliable and movable. In preferred embodiments of the present invention, the term refers to devices with plastic or vinyl enclosures.

As used herein, the term "rigid" refers to an item that is stiff (i.e., hard) and not pliable. In some embodiments of the present invention, the devices are composed of hard, non-pliable materials (e.g., some plastics).

As used herein, the term "iris membrane" refers to an iris diaphragm configuration. In preferred embodiments, the iris membrane functions to expand only to the desired size to allow the passage of a surgical means, etc. into or out of the controlled environment of the present invention. In some embodiments, the iris is composed of multiple overlapping flaps of material. However, in preferred embodiments, the iris membrane is composed of one piece of flexible material. The iris membrane of the present invention is flexible enough to allow the passage of a surgical means, but when coupled with the positive internal pressure of the CSE, prevents the leakage of air into the interior of the controlled environment of the present invention.

As used herein, the term "transport attachment" refers to either an integral portion of a CSE or CTE. In preferred embodiments, the CTE is attached to a CSE by means of a locking port, which prevents the introduction of air into either the CSE or the CTE. In embodiments in which the CTE is provided as an integral portion of a CSE, the CTE is detachably engaged to the CSE, such that it may be removed from the CSE as needed or desired. In particularly preferred embodiments, the transport attachment is useful for providing sterile, anaerobically prepared surgical instruments and transplant materials.

In summary, the present invention provides numerous advances and advantages over the prior art, including improved methods and devices for surgery performed under conditions to minimize oxidative damage to exposed tissues. All of these advantages enhance the surgical outcome when the device and methods of the present invention are used.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in surgical and other medical procedures, as well as transplant and grafting science, and/or related fields are intended to be within the scope of the following claims.

What is claimed is:

1. A method comprising:
    a) providing a device for maintaining an area in an isolated environment, said device comprising an enclosure for separating said area from an atmosphere ambient to said device, a means for evacuating said isolated environment, a means for refilling said isolated environment, and at least one access port, wherein said area is chosen from a surgical field and an injured area; and
    b) positioning the device over said area and releasably attaching said device to a patient's skin surrounding said area.

2. The method of claim 1, wherein said injured area is selected from the group consisting of burns, lesions, and broken bones.

3. The method of claim 1, wherein said at least one access port is suitable for admission of at least one surgical means selected from the group consisting of surgical instruments, robotics, sensors, and human hands.

4. The method of claim 1, further comprising step c) evacuating any gas within said isolated environment by using said means for evacuating.

5. The method of claim 4, further comprising step d) introducing sterile gas into said isolated environment by using said means for refilling.

6. The method of claim 5, wherein said means for refilling produces an environment with reduced oxygen tension.

7. The method of claim 5, wherein said means for refilling produces an environment with increased oxygen tension.

8. The method of claim 5, wherein said sterile gas is chosen from nitrogen, argon and a mixture thereof.

9. The method of claim 1, wherein said isolated environment is essentially pathogen-free.

10. A method comprising:
    a) providing a device for maintaining an area in an isolated environment, said device comprising an enclosure for separating said area from an atmosphere ambient to said device, a means for filling said isolated environment, and at least one access port, wherein said area is chosen from a surgical field and an injured area; and
    b) positioning the device over said area and releasably attaching said device to a patient's skin surrounding said area.

11. The method of claim 10, wherein said means for filling produces an environment with reduced oxygen tension.

12. The method of claim 10, wherein said means for filling produces an environment with an increased oxygen tension.

13. A method comprising:
    a) providing a device for maintaining and transporting transplant material in an isolated environment, said device comprising an enclosure for separating said transplant material from an atmosphere ambient to said device, a means for evacuating said isolated environment, a means for refilling said isolated environment, and an airlock for attaching said device to a controlled surgery environment, wherein the oxygen tension of said isolated environment is controllable;
    b) placing said transplant material in said device; and
    c) transporting said transplant material in said device to a transplant operation site.

14. The method of claim 13, wherein said means for evacuating comprises means for oxygen release and retention of a heavy gas within said isolated environment.

15. The method of claim 13, wherein said means for evacuating produces an environment with reduced oxygen tension.

16. The method of claim 13, wherein said means for refilling produces an environment with reduced oxygen tension.

17. The method of claim 13, wherein said means for refilling produces an environment with an increased oxygen tension.

18. The method of claim 13, wherein said isolated environment is essentially pathogen-free.

19. The method of claim 13, wherein said transplant material is selected from the group consisting of organs, tissues, cells, and artificial materials.

* * * * *